(12) United States Patent
Lahorkar et al.

(10) Patent No.: US 12,178,901 B2
(45) Date of Patent: Dec. 31, 2024

(54) POLYMER AND A TOPICAL COMPOSITION COMPRISING THE POLYMER

(71) Applicant: Conopco, Inc., Englewood Cliffs, NJ (US)

(72) Inventors: Praful Gulab Rao Lahorkar, Bangalore (IN); Shiyong Liu, Hefei (CN); Rajkumar Perumal, Erode (IN); Shengyu Shi, Hefei (CN); Ashish Anant Vaidya, Bangalore (IN); Chenzhi Yao, Hefei (CN); Xiaoxia Yang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 538 days.

(21) Appl. No.: 17/616,074

(22) PCT Filed: May 26, 2020

(86) PCT No.: PCT/EP2020/064506
§ 371 (c)(1),
(2) Date: Dec. 2, 2021

(87) PCT Pub. No.: WO2020/244960
PCT Pub. Date: Dec. 10, 2020

(65) Prior Publication Data
US 2022/0331225 A1     Oct. 20, 2022

(30) Foreign Application Priority Data

Jun. 4, 2019  (WO) ............... PCT/CN2019/090001
Jul. 2, 2019   (EP) ........................................ 19183810

(51) Int. Cl.
| | |
|---|---|
| *A61K 8/81* | (2006.01) |
| *A61Q 17/04* | (2006.01) |
| *A61Q 19/02* | (2006.01) |
| *C08F 220/36* | (2006.01) |
| *C08F 220/38* | (2006.01) |

(52) U.S. Cl.
CPC ............ *A61K 8/8152* (2013.01); *A61Q 17/04* (2013.01); *A61Q 19/02* (2013.01); *C08F 220/365* (2020.02); *C08F 220/387* (2020.02); *A61K 2800/54* (2013.01)

(58) Field of Classification Search
CPC ....... A61K 8/8152; A61Q 17/04; A61Q 19/02
See application file for complete search history.

(56) References Cited

U.S. PATENT DOCUMENTS

| | | |
|---|---|---|
| 3,887,603 A | 6/1975 | Rundberg, Jr. et al. |
| 6,869,598 B2 | 3/2005 | Love et al. |
| 6,956,013 B2 | 10/2005 | Dykstra et al. |
| 9,890,351 B2 | 2/2018 | Smets et al. |
| 2005/0020459 A1 | 1/2005 | Stowell |
| 2010/0324165 A1 | 12/2010 | Ritter et al. |
| 2011/0129540 A1 | 6/2011 | Chan et al. |
| 2012/0263807 A1 | 10/2012 | Horinek et al. |
| 2015/0274885 A1 | 10/2015 | Joy et al. |

FOREIGN PATENT DOCUMENTS

| | | |
|---|---|---|
| CN | 102604007 | 7/2012 |
| JP | 2017201891 | 11/2017 |
| RU | 2507216 | 2/2014 |
| RU | 2574030 | 1/2016 |
| SU | 650481 | 2/1979 |
| SU | 1122672 | 11/1984 |
| SU | 114101 | 2/1985 |
| WO | WO9907336 | 2/1999 |
| WO | WO2004043422 | 5/2004 |
| WO | WO2011064743 | 6/2011 |
| WO | WO2012104262 | 8/2012 |

OTHER PUBLICATIONS

Y.M. Kumar et al.; Structural and optical properties of VO2+ doped methacrylic acid ethylacrylate (MAA:EA) copolymer films; Materials Science—Poland; 36(1); pp. 34-41 (2018).
K.D. Lee et al.; Cisplatin-incorporated nanoparticles of poly(acrylic acid-co-methyl methacrylate) copolymer; International Journal of Nanomedicine; 8, pp. 2835-2845 (2013).
Search Report and Written Opinion issued in priority application EP19183810.1, dated Jan. 8, 2020 (6 pages).
Search Report and Written Opinion issued in PCT/EP2020/064506, dated Aug. 5, 2020 (12 pages).
Alaa S. Abo-El-Aziz, et al., "Benzo[f]- and Benzo[h]Coumarin-Containing Poly(methyl methacrylate)s and Poly(methyl methacrylate)s with Pendant Coumarin-Containing Azo Dyes", Macromolecular Chemistry and Physics, vol. 209, pp. 84-103 (2008).
R. Wang, et al., "A Molecular Interpretation on the Different Penetraion Enhancement Effect of Borneol and Menthol towards 5-Fluorouracil", Int. J. Mol. Sci., 18(12), pp. 1-12 (2017).

*Primary Examiner* — Andrew S Rosenthal
(74) *Attorney, Agent, or Firm* — Stephanie S. DelPonte

(57) ABSTRACT

The present invention relates to a polymer of formula I, a cosmetic composition comprising the polymer of formula I, a method of synthesizing the polymer of formula I; and use of the polymer of formula I to provide a benefit in a photoresponsive way.

13 Claims, 1 Drawing Sheet

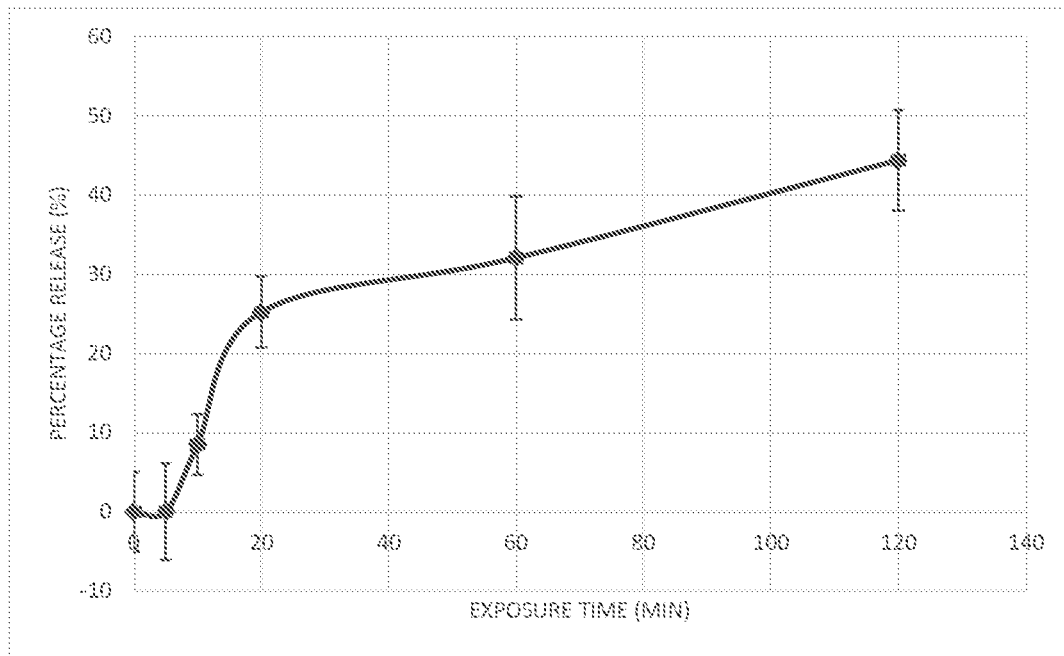

POLYMER AND A TOPICAL COMPOSITION COMPRISING THE POLYMER

CROSS REFERENCE TO RELATED APPLICATIONS

The present application is a U.S. National Phase Application under 35 U.S.C. § 371 of International Application No. PCT/EP2020/064506, filed on May 26, 2020, which claims priority to International Application No. PCT/CN2019/090001 filed Jun. 4, 2019, and European patent application No. 19183810.1 filed on Jul. 2, 2019, the contents of which are incorporated by reference herein in their entireties.

FIELD OF THE INVENTION

The present invention relates to a polymer and a cosmetic composition comprising the polymer.

BACKGROUND OF THE INVENTION

People often try to take care of themselves and of their body surfaces e.g. skin, scalp including hairs, axilla and oral cavity, with a desire of enjoying a healthy lifestyle. Some of the benefits people tend to have desire for include healthy and infection-free skin, even skin tone, adequate moisturization and protection from ultraviolet rays contained in sunlight.

Skin is the outermost protective covering of living beings and is the largest organ in the body. It acts as a barrier and protects the body from external factors e.g. dust, dirt, pollution and ultraviolet radiation contained in sunlight. Skin also helps prevent entry of harmful or potentially harmful microbes e.g. bacteria, fungi and viruses, from entering the body thereby preventing infection and/or other ill effects that may be caused. However, being the outermost covering, skin is always exposed to one or more factors mentioned earlier. As a result, skin is susceptible to developing one or more conditions e.g. dryness, wrinkles, loose/saggy skin, age spots, blotchy skin, melasma, freckle and increased pigmentation, which may lead to less preferred uneven skin tone.

One of the ways to reduce occurrence of such conditions is to avoid exposure to factors causing such conditions. However, in many instances, avoiding exposure to factors e.g. sunlight, is difficult and at times; unavoidable. For reasons like these, consumers tend to rely on cosmetic compositions comprising benefit agents that when applied on a surface of the human body e.g. skin, provide benefits such as moisturizing, anti-aging and skin lightening.

However, many if not all these benefit agents tend to either have relatively shorter shelf life and/or are spent within a short time after being applied on to a surface of the human body e.g. skin. Thus, benefit agents tend to be unavailable or be available in reduced amounts and/or activity when they are needed the most, thereby reducing a benefit to be delivered.

A few techniques are known in the art e.g. encapsulation and photoresponsive releases of a benefit agent, i.e. release of a benefit agent in response to exposure to light, thereby allowing a benefit agent to be available when it is required the most.

WO2012104262 (Universidad de Sevilla) discloses photoresponsive microcapsules comprising one or more first compartment(s) containing at least one sunscreen agent and one or more second compartment(s) containing a solvent or mixture of solvents for said sunscreen agent(s) but containing substantially no sunscreen agent(s) present in the first compartment(s) wherein the border between the first and second compartments becomes at least partially permeable for the sunscreen(s) and/or for the solvent or mixture of solvents upon exposure to an effective amount of UV radiation and/or radiation in the visible spectrum. Further subject matter relates to cosmetic and dermatological compositions containing the inventive microcapsules, methods for the preparation of the microcapsule and the compositions as well as to cosmetic and dermatological methods for protecting skin and/or hair against UV radiation using the compositions.

US20050020459 (Stowell) disclose fragrance compositions comprising a carrier solution used for cleaning purposes or for topical administration and nonfragrant photoresponsive agents that are capable of undergoing intramolecular photorearrangements to release a fragrance. The photoresponsive fragrance composition may comprise the prephotorearrangement first fragrance agent, the photorearranged and released fragrance agent, a combination of the first and second agents, or any of the above in combination with a known fragrance agent.

WO1999007336 (California Institute of Technology) discloses sunscreen compositions comprising a carrier for topical administration and photoresponsive first sunscreen agents which are capable of undergoing intramolecular photorearrangements to form second sunscreen agents. The second sunscreen agents absorb more ultraviolet radiation than the first sunscreen agents. The sunscreen composition may comprise the prephotorearrangement first sunscreen agent, the photorearranged second sunscreen agent, a combination of the first and second sunscreen agents, or any of the above in combination with a known sunscreen agent.

U.S. Pat. No. 6,956,013 (P&G) discloses a photo-activated pro-accord conjugate having a specific formula wherein [PHOTO] is a photo-labile unit which upon exposure to electromagnetic radiation is capable of releasing a pro-accord unit; X is a heteroatom selected from oxygen, nitrogen, sulfur; R1 and R2 are moieties when taken together comprise an aldehyde or a ketone fragrance raw material, and R3 comprises a fragrance raw material alcohol, amine, or thio compound.

However, the technique of encapsulation tends to suffer drawbacks e.g. capsules being susceptible to breaking due to mechanical force during transport and/or handling of compositions that comprise such capsules. In case of photoresponsive release of benefit agents, the prior art shows that benefit agents or their complexes formed with other chemicals undergo intramolecular rearrangement. These benefit agents as such, or their complex formed with other chemicals, are often smaller molecules that they tend to show good transdermal delivery (TDD) and get easily absorbed in the skin. For example, when a benefit agent e.g. menthol, is applied on to the skin of a consumer, it provides cooling effect. However, such cooling effect is obtained whether it is required at that time or not. In addition, menthol is a known penetration enhancer in the context of transdermal delivery (Wang et al; 2017, Int. J. Mol. Sci. 18 (12) 2747).

In either way, a benefit agent remains unavailable or remains available in reduced amounts and/or activity when it is required the most, thereby delivering reduced benefit to a consumer.

Need therefore exists to provide a solution to this problem so that a benefit agent remains available to provide a benefit when it is required the most. Need also exists to provide a solution so that a benefit agent remains available in expected amounts/activity to provide maximum benefit to a consumer.

A novel polymer has now been found to which a benefit agent is chemically attached along with a light absorbing moiety which releases a benefit agent upon exposure to light. The polymer, by virtue of its structure, resists transdermal delivery and is not easily absorbed in to the skin, thereby remaining available to providing a benefit when it is required the most.

SUMMARY OF THE INVENTION

In a first aspect, the present invention relates to a polymer according to formula I

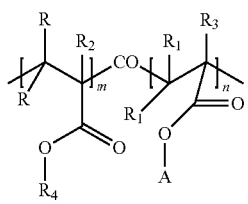

Formula I wherein,
$R=R_1=H$ or carbon atoms in the range from 1 to 2,
$R_2=R_3=H$ or carbon atoms in the range from 1 to 5,
$A=L-PR-L_1-B$ wherein,
$L=-R_5-NH-COO-R_6-R_7$ or $-R_5-COO-R_6-R_7$ wherein,
$R_5$ is carbon atom in the range from 1 to 6,
$R_6$ is carbon atom in the range 1 to 4,
$R_7$ is sulphur; or $R_7$ is a triazine linked to $-CH_2-CH_2-N(CH_2-CH_3)-$,
PR is a photoresponsive substance,
$L_1$ is carbonate linker,
B is a benefit agent,
$R_4$ is A; or $R_4$ is a group selected from $-[CH_2-CH_2-O-]_x$, $-[CH_2-CH(R)-O-]_x$ and mixtures thereof, where x is in the range from 1 to 10;
m=1 to 10,000; and n=1 to 10,000; and
wherein the photoresponsive substance is selected from the group consisting of a coumarin compound and a hydroquinone compound.

In a second aspect, the present invention relates to a cosmetic composition comprising the polymer according to formula I.

In a third aspect, the present invention relates to use of the polymer according to formula I in a composition for providing a benefit to the skin in a photoresponsive way.

BRIEF DESCRIPTION OF THE DRAWING

The FIGURE shows a graph of photo responsive release of menthol over time as described in Example 5.

DETAILED DESCRIPTION OF THE INVENTION

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "x to y", it is understood that all ranges combining the different endpoints are also contemplated. Unless specified otherwise, amounts as used herein are expressed in percentage by weight based on total weight of the composition and is abbreviated as "wt %". The use of any and all examples or exemplary language e.g. "such as" provided herein is intended merely to better illuminate the invention and does not in any way limit the scope of the invention otherwise claimed.

The Polymer According to the Present Invention

The polymer according to the present invention is a polymer of formula I

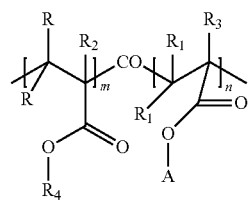

formula I wherein,
R is H or carbon atoms in the range from 1 to 2, preferably, R is H atom,
$R_1$ is H or carbon atoms in the range from 1 to 2, preferably, $R_1$ is H atom,
$R_2$ is H or carbon atoms in the range from 1 to 5, preferably, $R_2$ is carbon atoms in the range of 1 to 2,
$R_3$ is H or carbon atoms in the range from 1 to 5, preferably, $R_3$ is carbon atoms in the range of 1 to 2,
A is $L-PR-L_1-B$ wherein,
L is $-R_5-NH-COO-R_6-R_7$ or $-R_5-COO-R_6-R_7$, preferably L is $-R_5-NH-COO-R_6-R_7$; wherein,
$R_5$ is carbon atom in the range from 1 to 6,
$R_6$ is carbon atom in the range 1 to 4,
$R_7$ is sulphur; or $R_7$ is a triazine linked to $-CH_2-CH_2-N(CH_2-CH_3)-$,
PR is a photoresponsive substance selected from the group consisting of a coumarin compound and a hydroquinone compound. Preferably the photoresponsive substance is a coumarin compound. Both, a coumarin compound and a hydroquinone compound may be substituted or unsubstituted.
$L_1$ is carbonate linker,
B is a benefit agent preferably selected from a cooling agent, a fragrance, an antimicrobial agent and mixtures thereof. Preferred examples of cooling agent that may be used as a benefit agent include menthol. Preferred examples of fragrance that may be used as a benefit agent include santalol, linalool, nerol, citronellal. Preferred examples of an antimicrobial agent that may be used as a benefit agent include thymol and terpineol.
$R_4$ is A; or $R_4$ is a group selected from $-[CH_2-CH_2-O-]_x$, $-[CH_2-CH(R)-O-]_x$ and mixtures thereof, where x is in the range from 1 to 10, preferably, x is in the range from 1 to 5.

m=1 to 10,000 preferably 1 to 5,000 more preferably 1 to 1000; and n=1 to 10,000, preferably 1 to 5,000, more preferably 1 to 1,000.

A composition according to present invention (the composition) is a cosmetic composition that comprises a polymer according to the present invention. The composition preferably comprises from 0.001 to 10 wt %, more preferably from 0.01 to 8 wt %, even more preferably from 0.1 to 6 wt %, further more preferably from 0.1 to 4 wt % and still more preferably from 1 to 3 wt % of a polymer according to the present invention.

Preferably, the composition further comprises UVA organic sunscreens that absorbs UVA radiations and prevent them from reaching a surface e.g. skin of a user.

Examples of UVA organic sunscreens that may be used in the composition include dibenzoyl methane compound, bis-disulizole disodium (commercially available as Neo Heliopan® AP), diethylamino hydroxy benzoyl hexyl benzoate (commercially available as Uvinul® A Plus), Ecamsule (commercially available as Mexoryl SX) and Methyl anthranilate and also the class of water soluble sunscreens e. g. benzophenone-4, Bisdisulizole disodium and disodium phenyl do benzimidazole tetrasulphonate Preferably, UVA organic sunscreen that may be used as UVA sunscreen in the composition is selected from a dibenzoylmethane compound. Examples of sunscreen of dibenzoyl methane compound that may be used as UVA organic sunscreen in the composition include 4-tert-butyl-4'-methoxydibenzoylmethane (BMDM; commercially available as Parsol® 1789 or Avobenzone), 2-methyldibenzoyl-methane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoyl-methane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane.

Most preferably, dibenzoylmethane compound that may be used as UVA organic sunscreen is BMDM.

When incorporated in the composition, UVA organic sunscreens may preferably be incorporated from 0.01 to 10 wt %, more preferably from 0.1 to 7 wt %, even more preferably from 1 to 5 wt %, further more preferably from 1 to 3.5 wt %, yet more preferably 1 to 3 wt %, still more preferably 1 to 2.5 wt % in the composition.

Preferably, the composition further comprises UVB organic sunscreens that absorbs UVB radiations and prevent them from reaching a surface e.g. skin of a user.

Examples of UVB organic sunscreens that may be used in the composition include compounds from the class of cinnamic acid, salicylic acid, diphenyl acrylic acid and derivatives thereof. Examples of such compounds include 2-ethylhexyl salicylate (commercially available as Octisalate™), 3,3,5-Trimethylcyclohexyl 2-hydroxybenzoate (commercially available as Homosalate™), Ethylhexyl Methoxycinnamate (commercially available as NeoHelipan® AV), 2-ethylhexyl 2-cyano-3,3-diphenylacrylate (OCR; commercially available as Octocrylene™), 2-Hydroxy-4-methoxy-benzophenone (commercially available as Oxybenzone™), 2-ethyl-hexyl-4-methoxy cinnamate (MCX; commercially available as Parsol MCX™) and mixtures thereof. Examples of water soluble UVB organic sunscreens include phenyl benzimidazole sulphonic acid.

Preferably, UVB organic sunscreens that may be used in the composition are selected from OCR, MCX and mixtures thereof.

When incorporated in the composition, UVB organic sunscreens may preferably be incorporated from 0.01 to 10 wt %, more preferably from 0.1 to 7 wt %, even more preferably from 1 to 5 wt %, further more preferably from 1 to 3.5 wt %, yet more preferably from 1 to 3 wt %, still more preferably 1 to 2.5 wt % in the composition.

Preferably, the composition further comprises one or more skin lightening agents. These skin lightening agents may be selected from niacinamide, vitamin B6, vitamin C, vitamin A, glutathione precursors, resorcinol, phenylethyl resorcinol, 4-alkyl substituted resorcinol e.g. butyl resorcinol, hexyl resorcinol, glabridin, galardin, adapalene, aloe extract, ammonium lactate, arbutin, azelaic acid, butyl hydroxy anisole, butyl hydroxy toluene, citrate esters, deoxyarbutin, 1,3-diphenyl propane derivatives, 2,5-dihydroxy-benzoic acid and its derivatives, 2-(4-acetoxyphenyl)-1,3-dithiane, 2-(4-hydroxyphenyl)-1,3-dithiane, ellagic acid, gluco pyranosyl-1-ascorbate, gluconic acid, glycolic acid, green tea extract, 4-Hydroxy-5-methyl-3[2H]-furanone, 4-hydroxyanisole and its derivatives, 4-hydroxybenzoic acid derivatives, hydroxycaprylic acid, inositol ascorbate, lactic acid, lemon extract, linoleic acid, magnesium ascorbyl phosphate, 5-octanoyl salicylic acid, salicylic acid, 3,4,5-trihydroxybenzyl derivatives, acetylglucosamine, pitera extract, symwhite, calcium pantothenate (Melano-block), seppiwhite, soybean extract (bowman birk inhibitor), 12-hydroxystearic acid and mixtures thereof. When used in the composition, 12-hydroxystearic acid is used as a skin lightening agent and not as a fatty acid.

Preferably, skin lightening agents that may be used in the composition are selected from the group consisting of niacinamide, vitamin B6, 12-hydroxystearic acid, glutathione precursors, glabridin, galadrin, 4-alkyl substituted resorcinol and mixtures thereof.

The alkyl group in 4-alkyl substituted resorcinol can be straight chain alkyl or branched chain alkyl. For example, the alkyl group can be straight chain alkyl as in the case of 4-propyl resorcinol or it can be a branched chain alkyl like as in the case of 4-isopropyl resorcinol. Examples of 4-alkyl substituted resorcinol include 4-methyl resorcinol, 4-ethyl resorcinol (ER), 4-propyl resorcinol, IPR, 4-butyl resorcinol, 4-pentyl resorcinol, 4-hexyl resorcinol (HR), 4-heptyl resorcinol, 4-octyl resorcinol and mixtures thereof. Preferred 4-alkyl substituted resorcinol are ER, HR and mixtures thereof.

When incorporated in the composition, one or more skin lightening agents may preferably be present in an amount from 0.001 to 15 wt %, more preferably from 0.01 to 10 wt %, even more preferably from 0.1 to 5 wt %, further more preferably from 0.25 to 5 wt %, in the composition.

Preferably, the composition further comprises fatty acid. Fatty acids when present in a composition along with a soap provides the so called vanishing cream effect, i.e. a composition, when applied on to the human skin, vanishes on the skin leaving behind no significant streaks of the composition.

Preferably, the composition comprises fatty acids having carbon atoms in the range from 10 to 30, more preferably from 12 to 25, even more preferably from 14 to 20, further more preferably from 16 to 18.

Examples of fatty acids that may be used in the composition include pelargonic, lauric, myristic, palmitic, stearic, isostearic, oleic, linoleic, arachidic, behenic, erucic acid and mixtures thereof.

Preferably, the fatty acid that may be used is stearic acid or palmitic acid or a mixture thereof. The fatty acid in the present invention is preferably hystric acid which is substantially (generally about 90 to 95%) a mixture of stearic acid and palmitic acid in a ratio of between 55:45 to 45:55.

When incorporated in the composition, fatty acids may preferably be present in amounts from 4 to 25 wt %, more preferably 6 to 22 wt %, even more preferably 8 to 20 wt %, further more preferably 10 to 19 wt % and still more preferably 12 to 18 wt %.

Preferably, the composition further comprises soap. Soap when present in combination with fatty acid in the composition provides vanishing effect.

Soap of the invention is generally prepared by in-situ neutralization of fatty acid present in the composition. Thus, it is preferred that the soap has a carbon chain length that corresponds to the chain length of fatty acid in the composition. The soap is formed from the fatty acid through use of alkali metal hydroxides e.g. sodium hydroxide or potassium hydroxide. Of the two, potassium hydroxide is more preferred. Thus, the soap is preferably a potassium soap (potassium salt of fatty acid).

When incorporated in the composition, soap may preferably be present in amounts from 0.1 to 10 wt %, more preferably from 1 to 8 wt %, even more preferably from 2 to 7 wt %; and further more preferably from 3 to 6 wt %.

Preferably, the composition further comprises a nonionic surfactant having hydrophilic lipophilic balance (HLB) value in the range from 9 to 20, preferably from 10 to 19, more preferably from 12 to 18, even more preferably from 13 to 17 and yet more preferably from 15 to 17.

HLB is calculated using the Griffin method wherein HLB=20×Mh/M wherein Mh is the molecular mass of the hydrophilic portion of the molecule and M is the molecular mass of the whole molecule, giving a result on an arbitrary scale of 0 to 20. Typical values for various surfactants are given below:

A value <10: Lipid soluble (water insoluble)
A value >10: Water soluble
A value from 4 to 8 indicates an anti-foaming agent
A value from 7 to 11 indicates a W/O (water in oil) emulsifier
A value from 12 to 16 indicates oil in water emulsifier
A value from 11 to 14 indicates a wetting agent
A value from 12 to 15 is typical of detergents
A value of 16 to 20 indicates a solubiliser or a hydrotrope.

Preferably, the nonionic surfactant having HLB value in the range from 9 to 20 is selected from fatty alcohol ethoxylates, alkyl phenol ethoxylates, polyoxyethylene sorbitan alkyl esters and mixtures thereof. Preferably, the nonionic surfactants are ones with at least 9 alkylene oxide groups preferably at least 9 ethylene oxide groups.

Examples of fatty alcohol ethoxylates that may be used as nonionic surfactants in the composition include polyoxyethylene lauryl ether (HLB=16.9; commercially available as Brij® 35), polyoxyethylene (20) cetyl ether (HLB=16; commercially available as Brij® 58), polyethylene glycol octadecyl ether (HLB=18.8; commercially available as Brij® 700) and Laureth-9 (C12EO9; HLB=14.3; commercially available as Brij® L9).

Examples of alkyl phenol ethoxylates that may be used as nonionic surfactant in the composition include octylphenol ethoxylate (HLB=15.5; commercially available as Triton™ X165), octylphenol ethoxylate (HLB=17.6; commercially available as Triton™ X405) and octylphenol ethoxylate (HLB=18.4; commercially available as Triton™ X705).

Examples of polyoxyethylene sorbitan alkyl esters that may be used as the nonionic surfactant in the composition include polyoxyethylenesorbitan monolaurate (HLB=13.3; commercially available as Tween® 21), polyoxyethylene-sorbitan monolaurate (HLB=16.7; commercially available as Tween® 20), Polyoxyethylenesorbitan monopalmitate (HLB=15.6; commercially available as Tween® 40) and polyoxyethylene sorbitan monostearate (HLB=14.9; commercially available as Twee® 60).

More preferably, the nonionic surfactant having HLB value in the range from 9 to 20 that may be present in the composition is fatty alcohol ethoxylate with saturated carbon chain having HLB higher than 15.5.

Preferably, the composition comprises 0.5 to 5 wt %, more preferably 1 to 4 wt %, even more preferably from 2 to 3 wt % nonionic surfactant having HLB in the range from 9 to 20.

Preferably, the composition further comprises one or more polymers other than the polymer of the first aspect. These polymers act as thickener in the composition and improves sensorial properties of the composition. The polymer is preferably selected from the following classes:

acrylate/R-methacrylate copolymer e.g. acrylates/steareth-20 methacrylate copolymer (commercially available as Aculyn™ 22) and acrylates/beheneth-25 methacrylate copolymer (commercially available as Aculyn™ 28), acrylate/R-methacrylate crosspolymer e.g. acrylates/steareth-20 methacrylate crosspolymer (commercially available as Aculyn™ 88), acrylates copolymer (commercially available as Aculyn™ 33), acrylate/R-alkyl acrylate crosspolymer e.g. acrylates/C10-C30 alkyl acrylate crosspolymer (commercially available as Pemulen™ TR-2), copolymer of ammonium acryloyldimethyltaurate with vinyl pyrrolidone (commercially available as Aristoflex® AVC), copolymer of sodium acryloyldimethyltaurate with vinyl pyrrolidone (commercially available as Aristoflex® AVS); and crosspolymer of acryloyldimethyltaurate with R-alkyl acrylate and methylacrylate e.g. Ammonium acryloyldimethyltaurate/beheneth-25 methacrylate crosspolymer (commercially available as Aristoflex HMB and Aristoflex BLV).

Preferably, the composition comprises from 0.1 to 5 wt %, more preferably from 0.5 to 4.5 wt %, even more preferably from 1 to 4 wt %, further more preferably from 1.5 to 3.5 wt %, still more preferably from 2 to 3 wt % of a polymer other than the polymer of the first aspect.

Preferably, the composition comprises a cosmetically acceptable vehicle that includes water. Preferably, a cosmetically acceptable vehicle may be present in the composition in an amount from 5 to 99.9 wt %, more preferably from 10 to 95 wt %, even more preferably from 15 to 90 wt %, further more preferably from 20 to 80 wt %, still more preferably from 25 to 75 wt %; and yet more preferably from 30 to 70 wt %.

Preferably, the composition further comprises one or more thickening agents. Examples of thickening agents that may be incorporated in the composition include, Polyacrylates (such as Carbomers including Carbopol® 980, Carbopol® 1342 and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose).

Preferably, the composition further comprises solvents. Examples of solvents that may be used in the composition include ethyl alcohol, isopropanol, acetone, ethylene glycol monoethyl ether, diethylene glycol monobutyl ether, diethylene glycol monoethyl ether and mixtures thereof.

Preferably, the composition comprises thickeners in an amount ranging from 0.05 to 10 wt %, more preferably from 0.3 to 2 wt %.

Preferably, the composition further comprises preservatives to protect against the growth of potentially harmful microorganisms. Examples of ingredients that may be used as preservatives in the composition include alkyl esters of para-hydroxybenzoic acid, hydantoin derivatives, propionate salts, and a variety of quaternary ammonium compounds. More preferably, ingredients that may be used as preservative in the composition are sodium benzoate, iodopropynyl butyl carbamate, methylisothiazolinone, iodopropynylbutylcarbamate, phenoxyethanol, methyl paraben, propyl paraben, imidazolidinyl urea, sodium dehydroacetate, ethylhexylglycerin, benzyl alcohol, alkane diols and mixtures thereof. The alkane diols that are suitable for use as preservative are $C_6$-$C_{12}$ alkanes that are vicinally substituted with hydroxy groups. Illustrative examples include 1,2-octane diol (caprylyl glycol), 2,3-octane diol, 1,2-nonane diol, 1,2-decane diol, 1,2-hexane diol, 3,4-octane diol, mixtures thereof or the like where caprylyl glycol is typically the most preferred.

When present in the composition, preservatives are added preferably in an amount from 0.001 to 5 wt %, more preferably from 0.01 to 3 wt % and most preferably from 0.02 to 2 wt %.

Preferably, the composition further comprises vitamins and flavonoids. Examples of vitamins include Vitamin $B_2$, Vitamin C, ascorbyl phosphate and Biotin, Vitamin A (retinol), Vitamin A Palmitate, ascorbyl tetraisopalmitate, sodium ascorbyl phosphate, Vitamin E (tocopherol), Vitamin E Acetate and DL-panthenol. A particularly suitable Vitamin $B_6$ derivative is Pyridoxine Palmitate. Examples of preferred flavonoids include glucosyl hesperidin and rutin.

Preferably, the composition comprises vitamins or flavonoids, collectively or individually in an amount from 0.001 to 10 wt %, more preferably from 0.01 to 5 wt %, and even more preferably from 0.1 to 3 wt %.

Preferably, the composition further comprises herbal extracts. Examples of herbal extracts include pomegranate, white birch (Betula Alba), green tea, chamomile, licorice, boswellia serrata, olive (Olea Europaea) leaf, arnica montana flower, *Lavandula angustifolia*, and extract combinations thereof. The extracts may either be water soluble or water-insoluble carried in a solvent which respectively is hydrophilic or hydrophobic. Water and ethanol are the preferred extract solvents.

Preferably, the composition further comprises a range of other optional ingredients that include binders, biological additives, buffering agents, colorants, astringents, fragrance, opacifying agents, conditioners, exfoliating agents, pH adjusters and skin healing agents.

The composition is preferably formulated in the form of a powder, flake, lotion, cream, gel or mousse. More preferably, the composition is formulated in the form of cream or lotion and most preferably in the form of cream. The composition can be a leave-on or wash-off type of composition. The composition is preferably a leave-on type of composition.

The packaging for the composition of this invention can be a patch, bottle, tube, roll-ball applicator, propellant driven aerosol device, squeeze container or lidded jar.

Further, the present invention also relates to a method of synthesizing the polymer of the first aspect.

The synthesis route was found to be dependent on the choice of photoresponsive substance (PR) selected from the group consisting of a coumarin compound and a hydroquinone compound, preferably a coumarin compound. Both, a coumarin compound and a hydroquinone compound may be substituted or unsubstituted.

Accordingly, a method of synthesizing the polymer of the first aspect wherein the photoresponsive substance is a coumarin compound, the method comprises the steps:

i. 7-amino 4-methyl coumarin (Compound 1) is reacted with Tosyl chloride (TsCl) in the presence of pyridine in dichloromethane (DCM) at 0° C. to obtain compound 2,

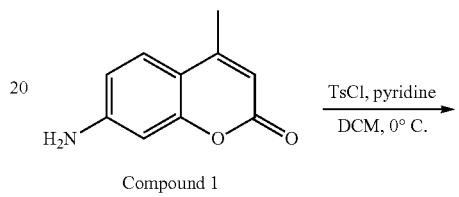

Compound 1

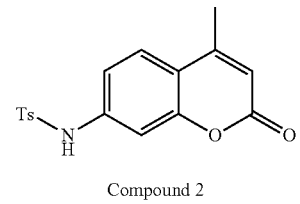

Compound 2 ii. Compound 2 is reacted with ethylene dibromide in presence of potassium iodide and cesium carbonate in acetonitrile ($CH_3CN$) at reflux conditions to obtain Compound 3,

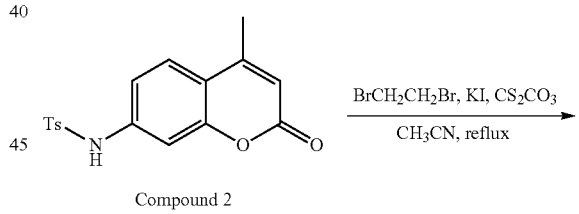

Compound 2

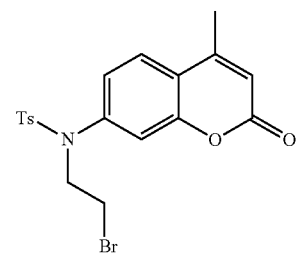

Compound 3 iii. Compound 3 is reacted with concentrated sulphuric acid at 0° C. to obtain compound 4,

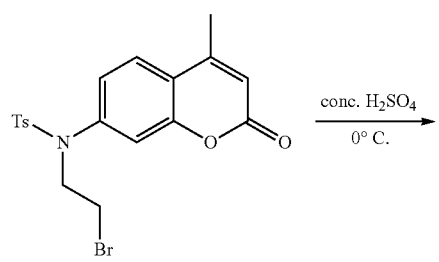

Compound 3

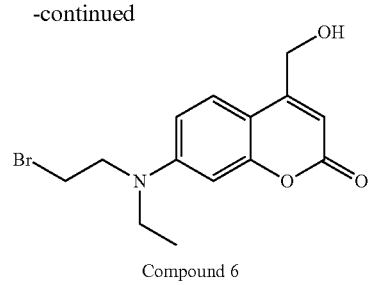

Compound 6 vi. Compound 6 is reacted with sodium azide (NaN₃) in presence of sodium iodide in N,N-Dimethylformamide solvent (DMF) to obtain compound 10,

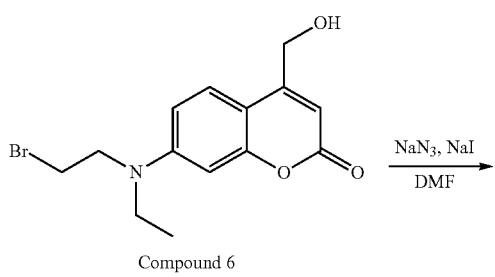

Compound 6

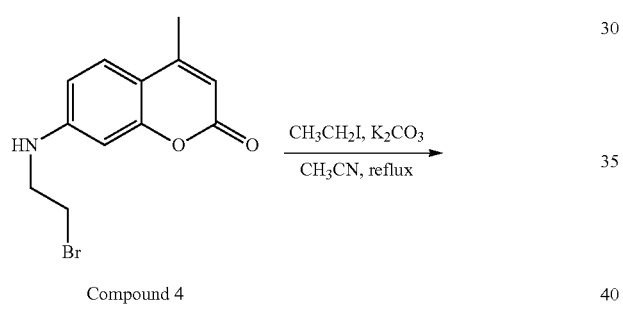

Compound 4 iv. Compound 4 is reacted with ethyl iodide in presence of potassium carbonate in acetonitrile (CH₃CN) under reflux conditions to obtain compound 5

Compound 4

Compound 5 v. Compound 5 is oxidized in the presence of selenium dioxide (SeO₂) in p-xylene under reflux condition and the resulting reaction mixture after workup procedures treated with reducing agent sodium borohydride in methanol to obtain compound 6,

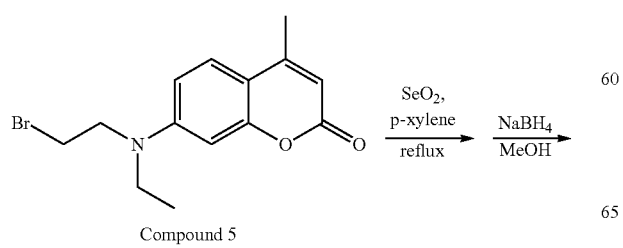

Compound 5

Compound 10 vii. Compound 7 is reacted with Compound 8 (propargyl alcohol) in presence of dibutyltin laurate (DBTL) in tetrahydrofuran (THF) to obtain compound 9,

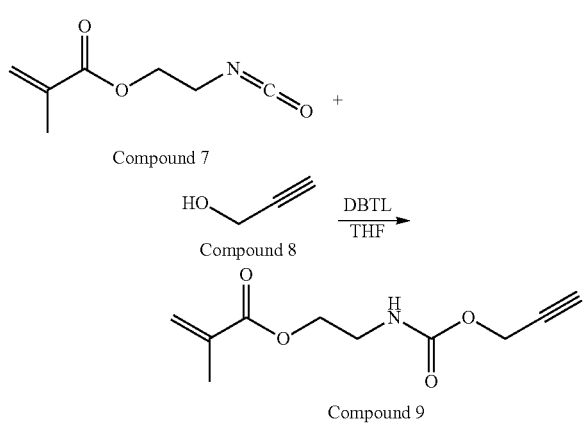

Compound 7

Compound 8

Compound 9

This step (vii) as described above may be carried out either before or after steps (i) to (vi) are carried out.

viii. Compound 9 is reacted with compound 10 in the presence of copper(I) bromide and pentamethyldiethylenetriamine (PMDETA) to obtain compound 11,

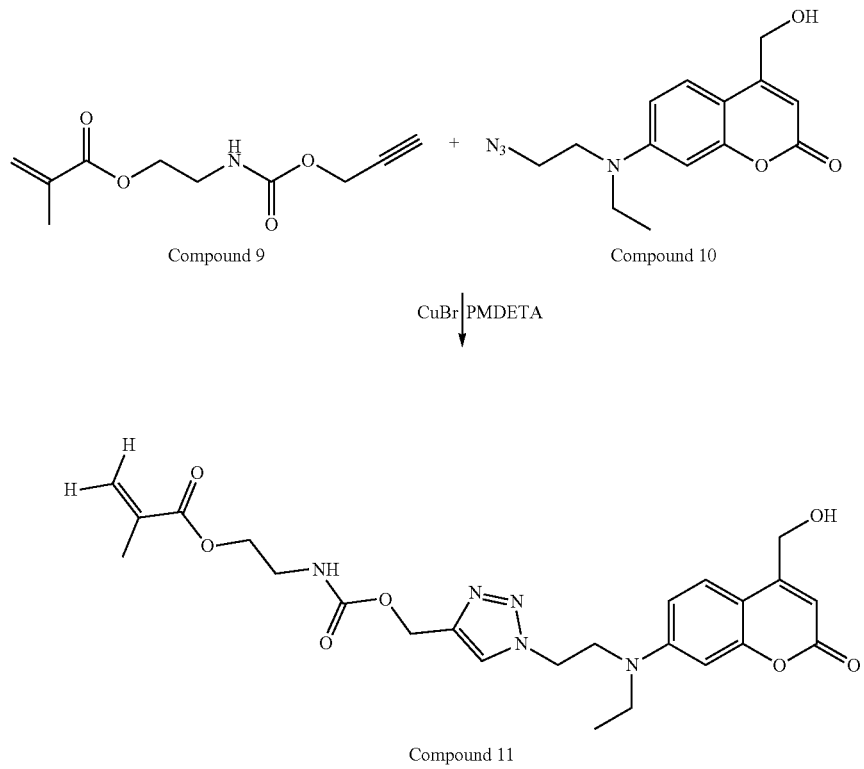

Compound 11 ix. Compound 12 (4-Nitrophenyl chloroformate) is reacted with a benefit agent (B) that may preferably be a cooling agent such as menthol, a fragrance compound such as santalol, linalool, nerol, citronellal, or an antimicrobial agent such as thymol or terpineol, in presence of 4-(Dimethylamino) pyridine (DMAP) in dichloromethane obtain compound 14,

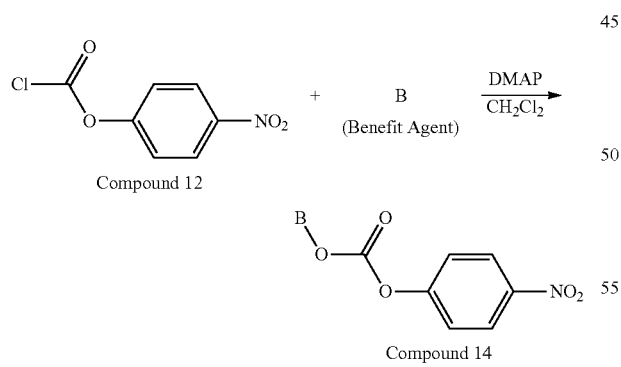

Compound 14

This step (ix) as described above may be carried out either before or after steps (i) to (vi), step (vii) and step (viii) are carried out.

x. Compound 14 is reacted with compound 11 in presence of 4-Dimethylaminopyridine (DMAP) in dichloromenthane (DCM) at room temperature to obtain compound 15,

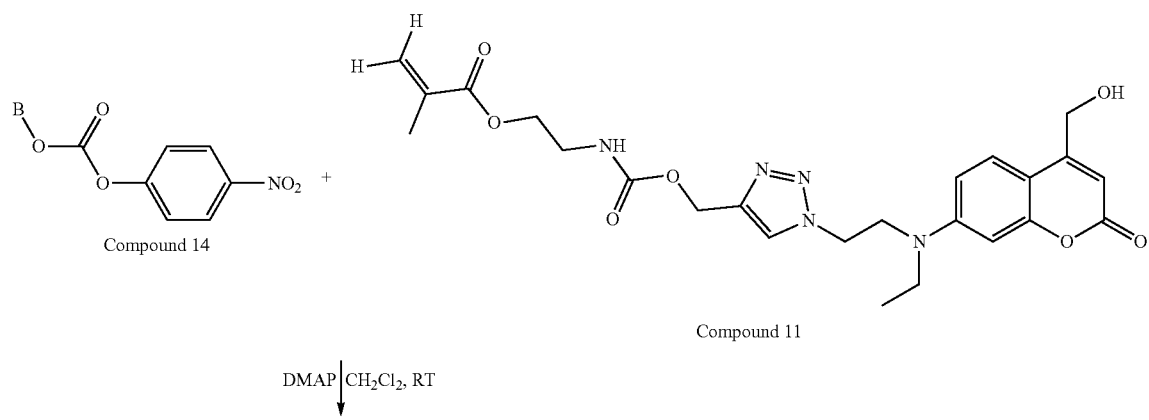
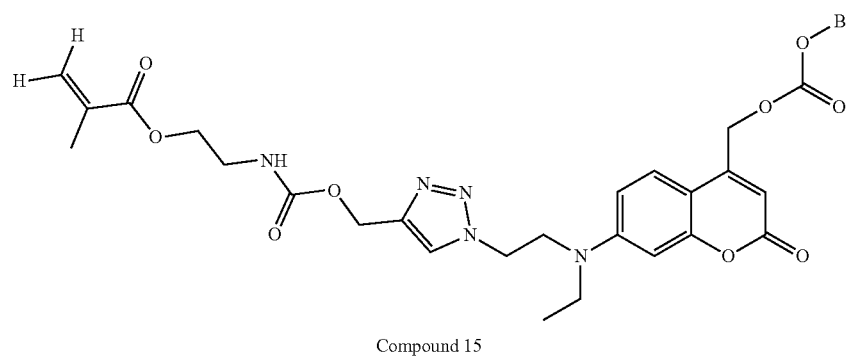
xi. Lastly, compound 15 and compound 16 are polymerised with the help of V-70(2,2'-Azobis(4-methoxy-2,4-dimethylvaleronitrile) in Tetrahydrofuran (THF) to obtain compound according to formula I.
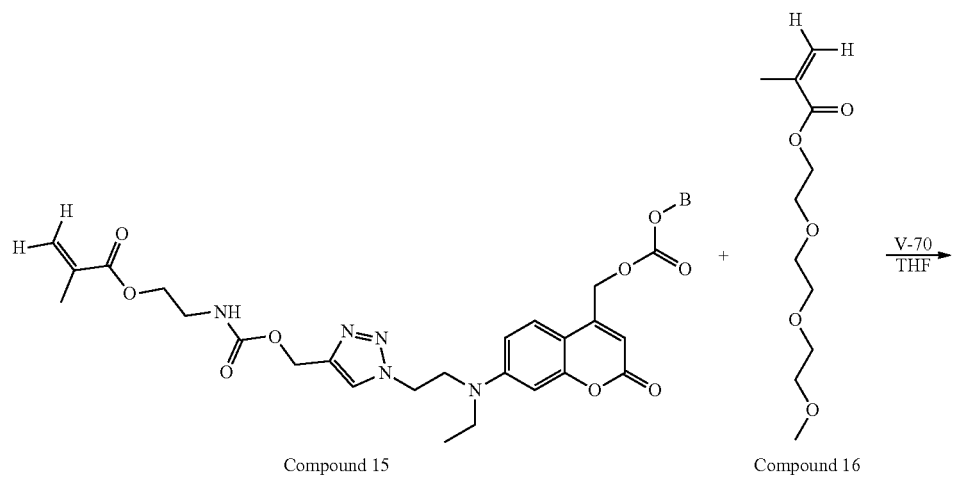

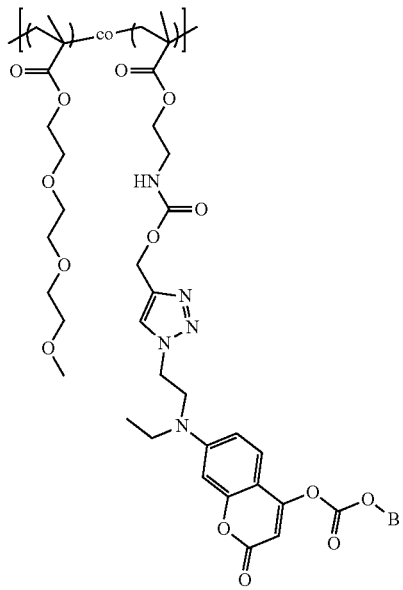

Compound according to formula I

Alternatively, a method of synthesizing the polymer of the first aspect wherein the photoresponsive substance is a hydroquinone compound, the method comprises the steps:

Step 1

2,5 dimethyl hydroquinone (compound 1h) is reduced with sodium borohydride in methanol to obtain compound 2h.

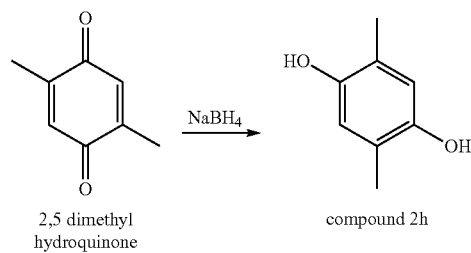

2,5 dimethyl hydroquinone          compound 2h

Step 2

Compound 2h is reacted with compound 3h to yield compound 4h.

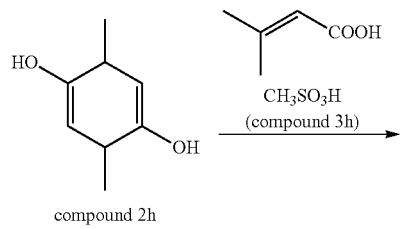

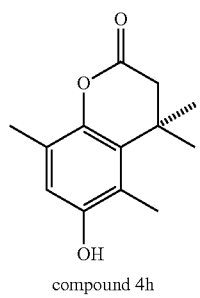

compound 4h

Step 3

Compound 4h is reacted with bromine in presence of acetic acid to obtain compound 5h.

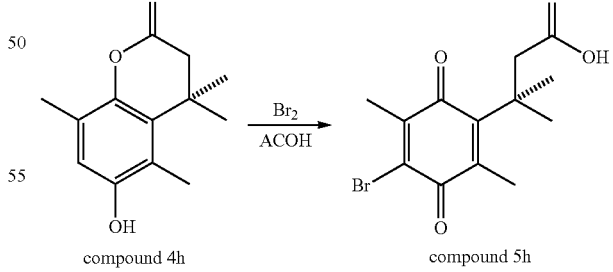

compound 4h          compound 5h

Step 4

Compound 5h is reacted with a benefit agent (B) that may preferably be a cooling agent such as menthol, a fragrance compound such as Santalol, Linalool, Nerol, Citronellal, or an antimicrobial agent such as thymol or terpineol, in presence of N-(3-Dimethylaminopropyl)-N'-ethylcarbodiimide (EDC·HCl.) and Dimethylaminopyridine (DMAP) to obtain compound 6h.

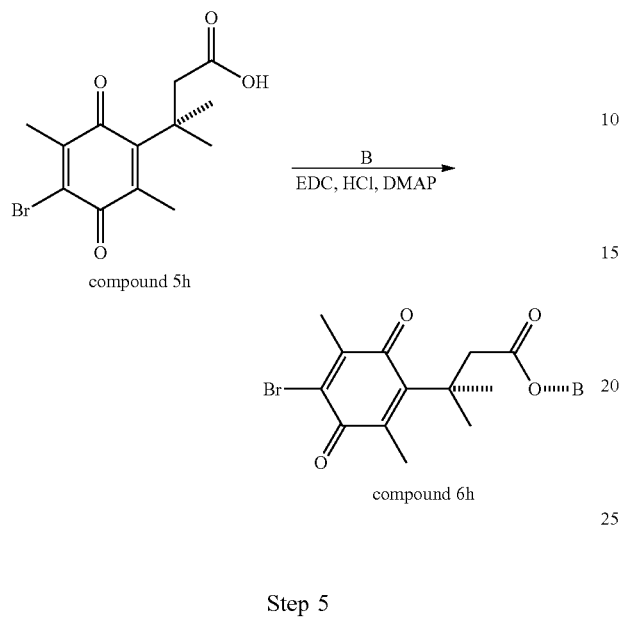

compound 5h compound 6h

Step 5

Compound 6h is reacted with 2-mercaptoethanol and potassium carbonate to obtain compound 7h.

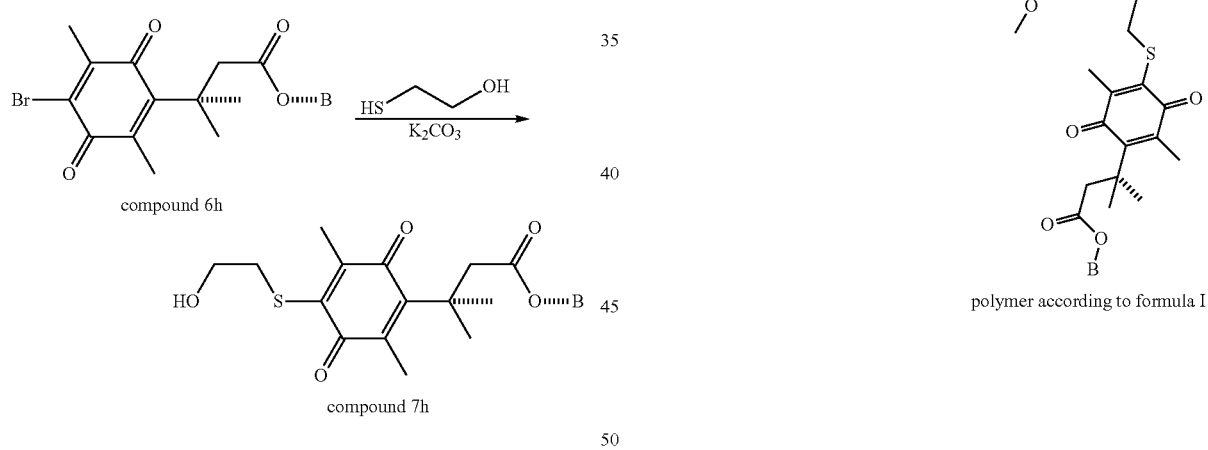

compound 6h compound 7h

Step 6

Compound 7h is reacted with Compound 8h to obtain the compound according to formula I.

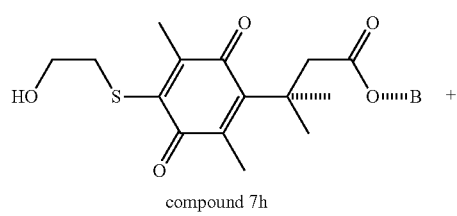

compound 7h

Compound 8h polymer according to formula I

In a third aspect, the present invention relates to use of the polymer according to formula I in a composition for providing a benefit in a photoresponsive way. It will be understood that a benefit that may be delivered will be based on a benefit agent selected. For example, if benefit agent is selected to be a cooling agent such as menthol, then cooling benefit is delivered. Likewise, fragrance will be delivered if the benefit agent is a fragrance molecule.

The following examples are provided to facilitate an understanding of the invention. The examples are not intended to limit the scope of the claims.

EXAMPLES
Example 1: A Polymer According to Formula I Wherein the Photoresponsive Substance is a Coumarin Compound
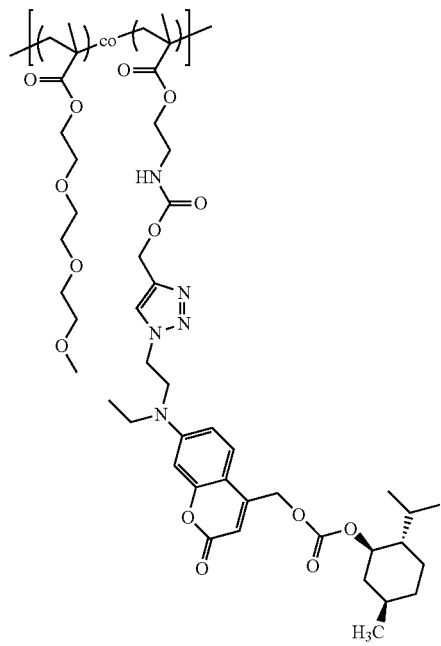
Example 2: A Polymer According to Formula I Wherein the Photoresponsive Substance is a Hydroquinone Compound
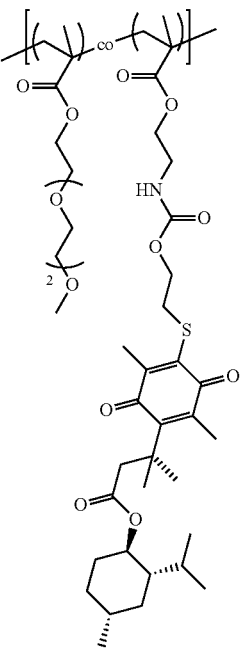
Example 3: A Polymer According to Formula I
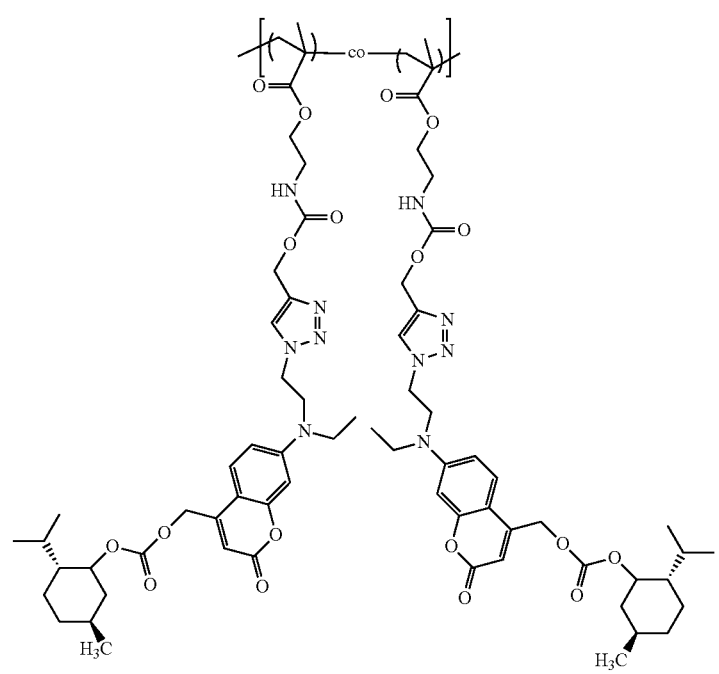

Example 4: A Cosmetic Composition Comprising the Polymer of the Invention

| Ingredients | Wt % |
|---|---|
| Glycerin | 1 |
| Disodium EDTA | 0.1 |
| Cetyl alcohol | 0.53 |
| Preservative | 0.5 |
| Isopropyl myristate | 0.75 |
| DC200 350 | 0.5 |
| Soap | 2 |
| Stearic acid | 17 |
| 4-tert-butyl-4'-methoxydibenzoylmethane | 1.2 |
| 2-ethyl-hexyl-4-methoxy cinnamate | 2.4 |
| Niacinamide | 3 |
| Water | to 100 |

Example 5: Quantification of Release of a Benefit Agent Upon Exposure to a Light Source Quantification of release of a benefit agent e.g. menthol was carried out as follows. 30 μL of menthol solution (100 ppm; L-Menthol; 99%, Sigma Aldrich) and 30 μL of the polymer according to formula I (100 ppm) were applied on HPTLC plates (HPTLC Silica Gel 60 F254 Plates from Merck) using Linomat 5 applicator and were exposed to light for up to 2 h (9 W LED light); and the plates were subjected to ascending chromatography (mobile phase Hexane (8): Ethyl acetate (2)). After derivatization in p-anisaldehyde solution the plates were scanned at 510-520 nm using a HPLTC instrument (CAMAG TLC Scanner 3) and measurement of peak area obtained were found to be as shown in the FIGURE.

Example 6: Synthesis of the Polymer According to Formula I Wherein the Photoresponsive Substance is a Coumarin Compound Where the photoresponsive substance was selected to be a coumarin compound, a polymer according to formula I was synthesized using the following steps:

i. 7-amino 4-methyl coumarin (Compound 1) is reacted with Tosyl chloride (TsCl) in the presence of pyridine in dichloromethane (DCM) at 0° C. to obtain compound 2,

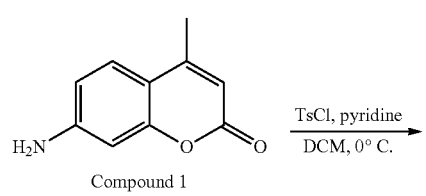

Compound 1

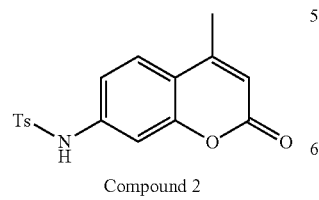

Compound 2 ii. Compound 2 is reacted with ethylene dibromide in presence of potassium iodide and cesium carbonate in acetonitrile (CH₃CN) at reflux conditions to obtain Compound 3,

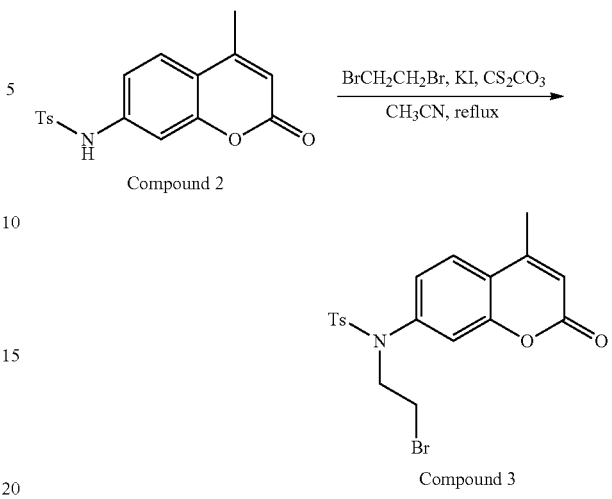

Compound 2

Compound 3 iii. Compound 3 is reacted with concentrated sulphuric acid at 0° C. to obtain compound 4,

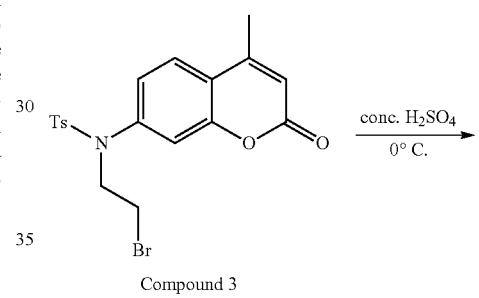

Compound 3

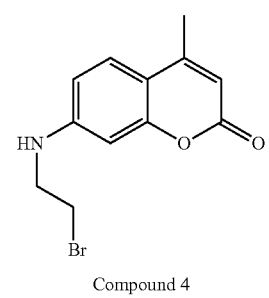

Compound 4 iv. Compound 4 is reacted with ethyl iodide in presence of potassium carbonate in acetonitrile (CH₃CN) under reflux conditions to obtain compound 5,

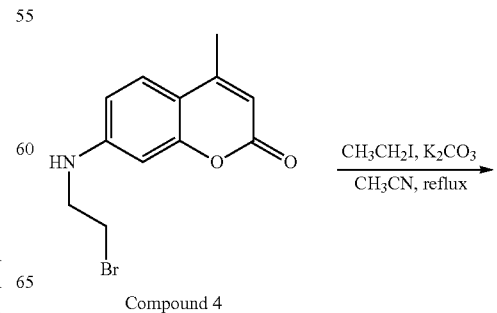

Compound 4

-continued

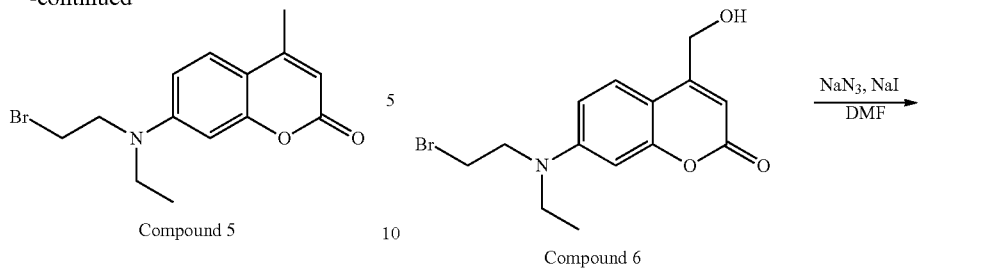

v. Compound 5 is oxidized in the presence of selenium dioxide (SeO$_2$) in p-xylene under reflux condition and the resulting reaction mixture after workup procedures treated with reducing agent sodium borohydride in methanol to obtain compound 6,

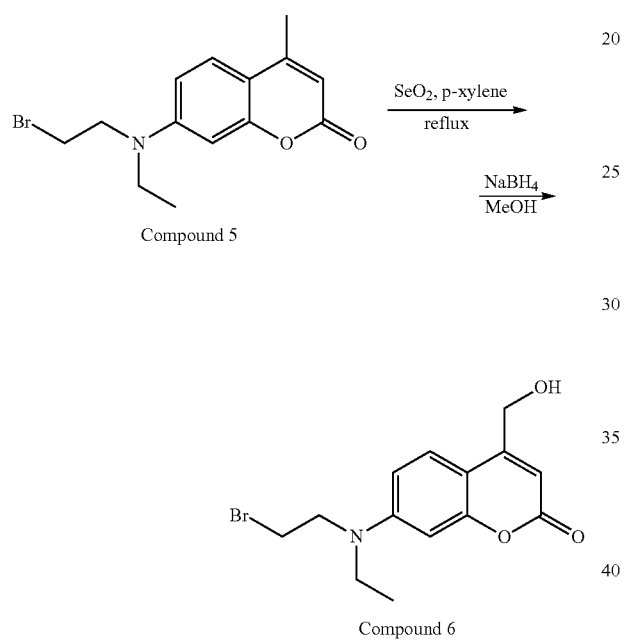

vi. Compound 6 is reacted with sodium azide (NaN$_3$) in presence of sodium iodide in N,N-Dimethylformamide solvent (DMF) to obtain compound 10, vii. Compound 7 is reacted with Compound 8 (propargyl alcohol) in presence of Dibutyltin laurate (DBTL) in Tetrahydrofuran (THF) to obtain compound 9, wherein step (vii) may be carried out either before or after steps (i) to (vi) are carried out, viii. Compound 9 is reacted with compound 10 in the presence of copper(I) bromide and pentamethyldiethylenetriamine (PMDETA) to obtain compound 11.

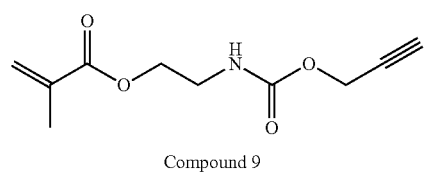

Compound 9

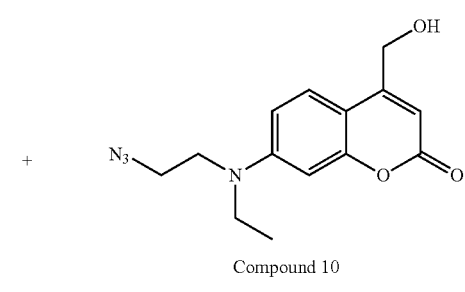

Compound 10

CuBr | PMDETA

-continued

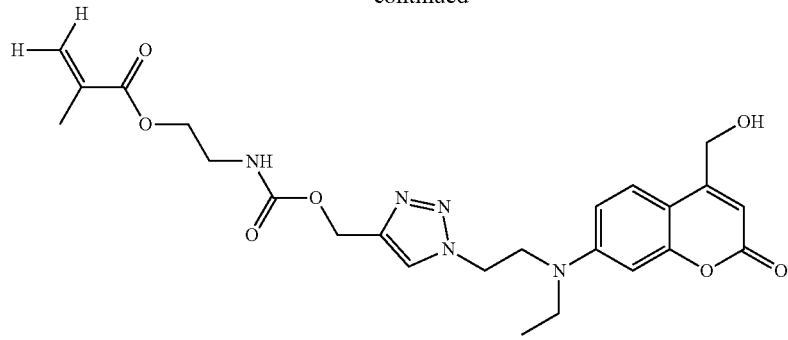

Compound 11 ix. Compound 12 (4-Nitrophenyl chloroformate) is reacted with menthol (a benefit agent B) in the presence of 4-(Dimethylamino) pyridine (DMAP) in dichloromethane obtain compound 14,

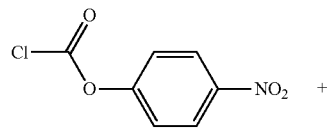

Compound 12

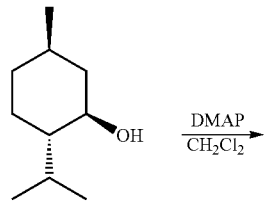

Compound 13

-continued

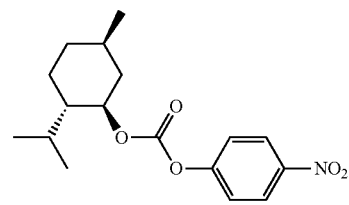

Compound 14 x. Compound 14 is reacted with compound 11 in presence of 4-Dimethylaminopyridine (DMAP) in dichloromenthane (DCM) at room temperature to obtain compound 15,

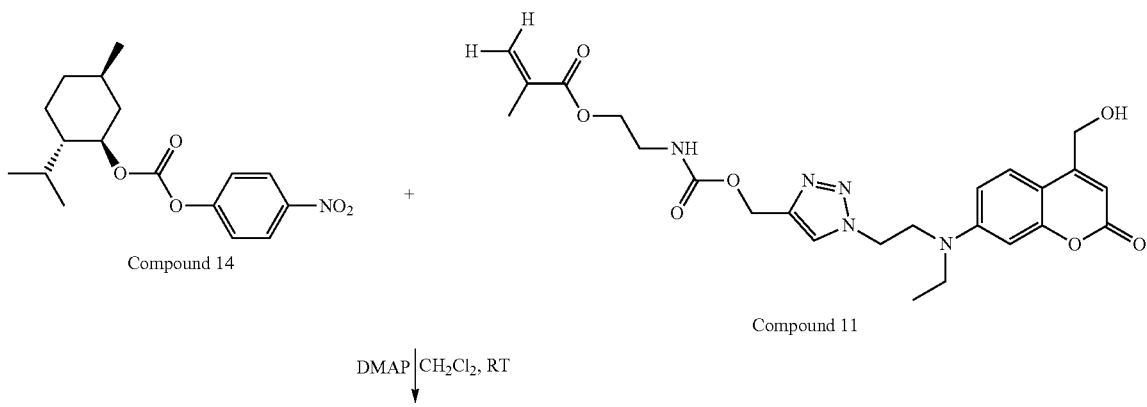

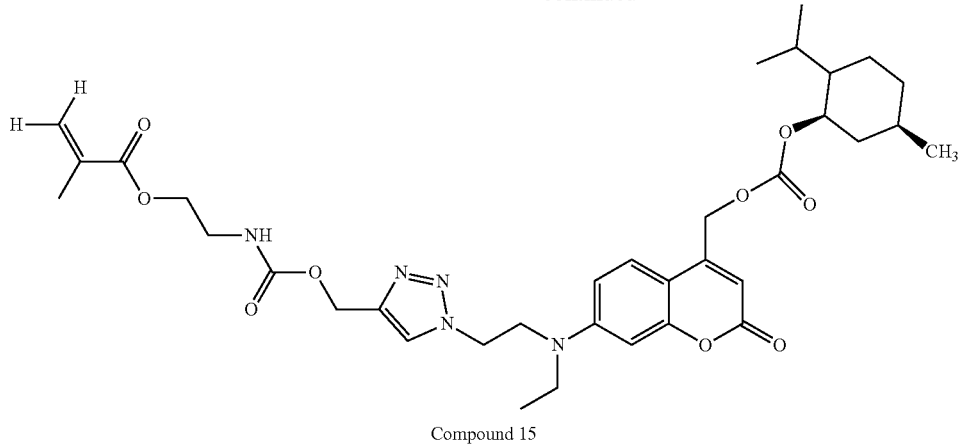
Compound 15
xi. Compound 15 and compound 16 are polymerised with the help of V-70(2,2'-Azobis(4-methoxy-2,4-dimethyl-valeronitrile) in Tetrahydrofuran (THF) to obtain a polymer according to formula I.
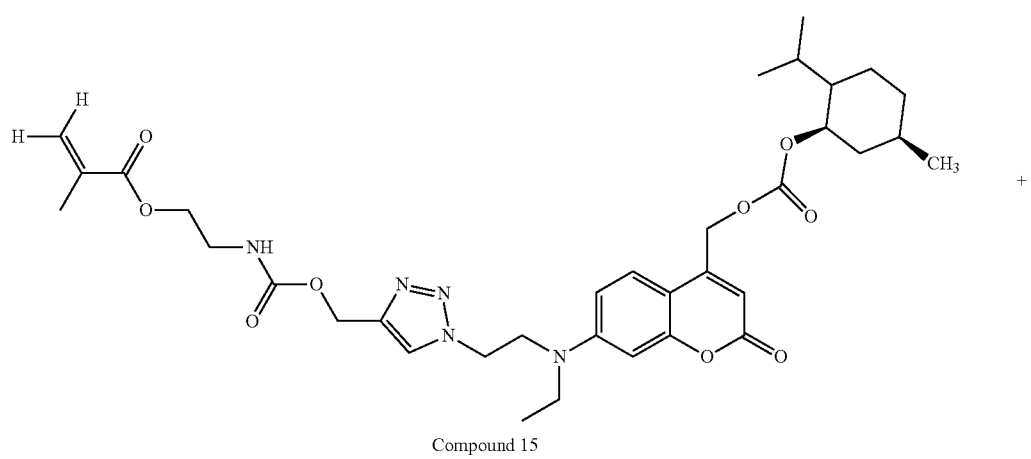
Compound 15

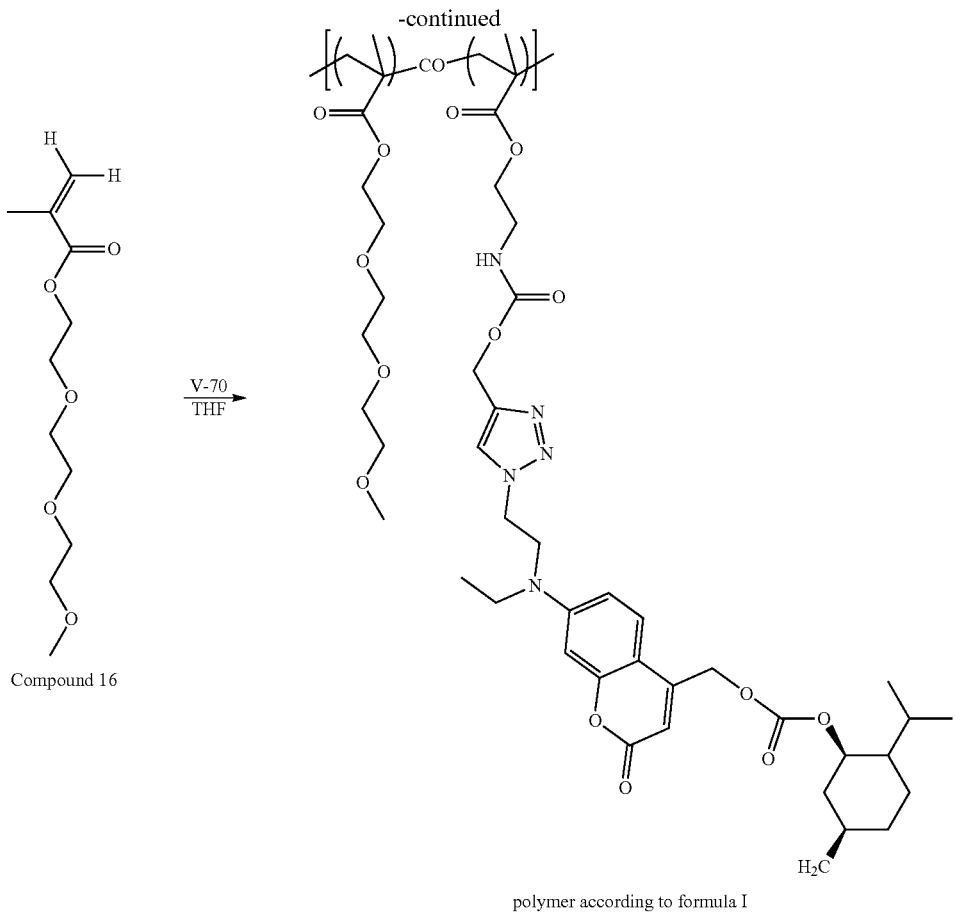

Compound 16 polymer according to formula I

Example 7: Synthesis of the Polymer According to Formula I wherein the Photoresponsive Substance is a Hydroquinone Compound Where the photoresponsive substance was selected to be a hydroquinone compound, a polymer according to formula I was synthesized using the following steps:

Step 1

2,5 dimethyl hydroquinone (compound 1h) is reduced with sodium borohydride in methanol to obtain compound 2h.

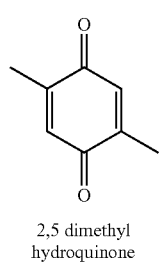

2,5 dimethyl hydroquinone

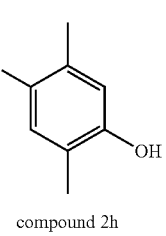

compound 2h

Step 2

Compound 2h is reacted with compound 3h to yield compound 4h.

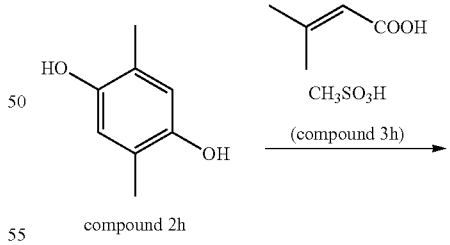

compound 2h

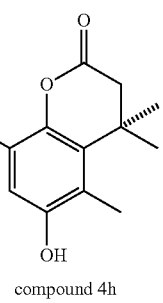

compound 4h

Step 3

Compound 4h is reacted with bromine in presence of Acetic acid to obtain compound 5h.

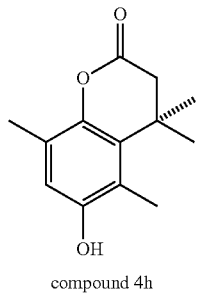

compound 4h

→ Br₂ / ACOH compound 5h

Step 4

Compound 5h is reacted with menthol (a benefit agent B), in presence of N-(3-Dimethylaminopropyl)-N'-ethylcarbodiimide (EDC·HCl.) and Dimethylaminopyridine (DMAP) to obtain compound 6h.

compound 5h + menthol → EDC, HCl, DMAP → compound 6h

Step 5

Compound 6h is reacted with 2-mercaptoethanol and potassium carbonate to obtain compound 7h.

compound 6h → HS-CH₂CH₂-OH / K₂CO₃ → compound 7h

Step 6

Compound 7h is reacted with Compound 8h to obtain the compound according to formula I.

compound 7h + Compound 8h → DBTL

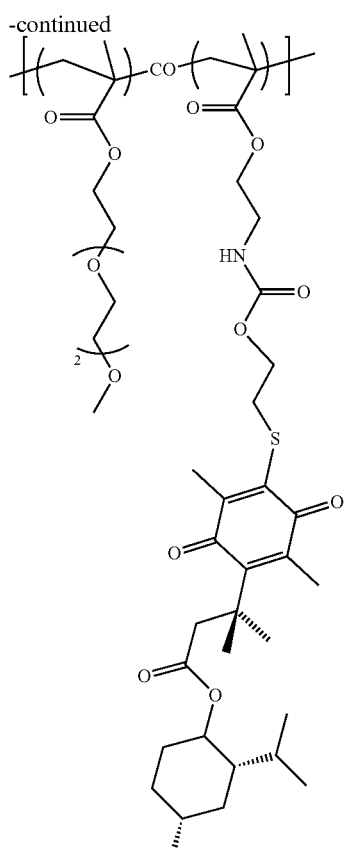

polymer according to formula I

The invention claimed is:

1. A polymer according to formula I

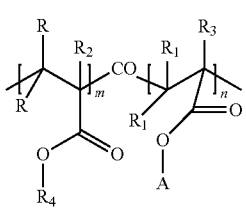

wherein, $R=R_1=H$ or carbon atoms in the range from 1 to 2,
$R_2=R_3=H$ or carbon atoms in the range from 1 to 5,
$A=L-PR-L_1-B$ wherein,
$L=-R_5-NH-COO-R_6-R_7$ or $-R_5-COO-R_6-R_7$ wherein,
$R_5$ is carbon atom in the range from 1 to 6,
$R_6$ is carbon atom in the range 1 to 4,
$R_7$ is sulphur; or $R_7$ is a triazine linked to $-CH_2-CH_2-N(CH_2-CH_3)-$,
PR is a photoresponsive substance,
$L_1$ is carbonate linker,
B is a benefit agent,
$R_4$ is A; or $R_4$ is a group selected from $-[CH_2-CH_2-O-]_x$, $-[CH_2-CH(R)-O-]_x$ and mixtures thereof, where x is in the range from 1 to 10;
m=1 to 10,000; and n=1 to 10,000; and
wherein the photoresponsive substance is selected from the group consisting of a coumarin compound and a hydroquinone compound.

2. The polymer according to claim 1, wherein $R_2$ or $R_3$ independently is carbon atoms in the range from 1 to 2.

3. The polymer according to claim 1, wherein $R_4=-[CH_2-CH_2-O-]_x$ where x is in the range from 1 to 5.

4. The polymer according to claim 1, wherein L is $-R_5-NH-COO-CH_3$-Triazine-$CH_2-CH_2-N(CH_2-CH_3)-$.

5. The polymer according to claim 1, wherein the benefit agent is selected from a cooling agent, a fragrance, an antimicrobial compound and mixtures thereof.

6. The polymer according to claim 1, wherein the polymer is:

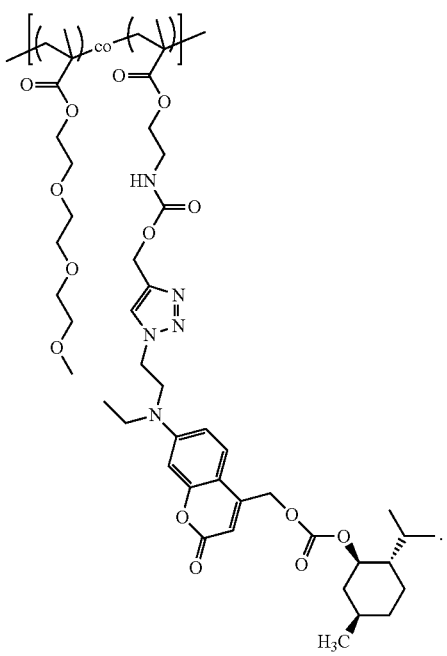

7. A cosmetic composition comprising the polymer as claimed in claim 1.

8. The composition according to claim 7 further comprising from 0.01 to 10 wt % UVA organic sunscreen.

9. The composition according to claim 7 further comprising from 0.01 to 10 wt % UVB organic sunscreen.

10. The composition according to claim 7 further comprising a skin lightening agent selected from the group consisting of niacinamide, vitamin B6, 12-hydroxystearic acid, glutathione precursors, galardin, 4-alkyl substituted resorcinol, and mixtures thereof.

11. The composition according to claim 7 further comprising from 4 to 25 wt % fatty acid.

12. The composition according to claim 7 further comprising from 0.1 to 10 wt % soap.

13. A method comprising incorporating the polymer according to claim 1 in a composition for providing a benefit to the skin in a photoresponsive way.

* * * * *